(12) United States Patent
Arbab et al.

(10) Patent No.: US 7,851,016 B2
(45) Date of Patent: Dec. 14, 2010

(54) ARTICLE HAVING NANO-SCALED STRUCTURES AND A PROCESS FOR MAKING SUCH ARTICLE

(75) Inventors: Mehran Arbab, Pittsburgh, PA (US); Deirdre D. Ragan, Clemmons, NC (US); Songwei Lu, Wexford, PA (US)

(73) Assignee: PPG Industries Ohio, Inc., Cleveland, OH (US)

(*) Notice: Subject to any disclaimer, the term of this patent is extended or adjusted under 35 U.S.C. 154(b) by 0 days.

(21) Appl. No.: 12/413,994

(22) Filed: Mar. 30, 2009

(65) Prior Publication Data

US 2009/0208648 A1    Aug. 20, 2009

Related U.S. Application Data

(63) Continuation of application No. 11/843,756, filed on Aug. 23, 2007, now abandoned, which is a continuation of application No. 10/623,401, filed on Jul. 18, 2003, now abandoned.

(60) Provisional application No. 60/397,486, filed on Jul. 19, 2002.

(51) Int. Cl.
*B05D 3/02* (2006.01)
(52) U.S. Cl. .................... 427/229; 427/226
(58) Field of Classification Search .......... 427/226, 427/229
See application file for complete search history.

(56) References Cited

U.S. PATENT DOCUMENTS 5,540,959 A * 7/1996 Wang .................. 427/561

FOREIGN PATENT DOCUMENTS

| FI | 98832 B | | 5/1997 |
|---|---|---|---|
| WO | 0020346 A1 | | 4/2000 |
| WO | 0128941 A1 | | 4/2001 |
| WO | 0246112 A1 | | 6/2002 |
| WO | WO02/46112 | * | 6/2002 |

* cited by examiner

*Primary Examiner*—Michael Cleveland
*Assistant Examiner*—Robert Vetere
(74) *Attorney, Agent, or Firm*—Andrew C. Siminerio

(57) ABSTRACT

A process for producing an article having modified optical, chemical, and/or physical properties is disclosed. The process includes (a) fluidizing a starting material; (b) forcing the fluidized starting material toward the article; and (c) passing the fluidized starting material through a high energy zone. The passing step can occur before the forcing step; after the forcing step but before the fluidizing material comes in contact with the surface of the article; and/or after the forcing step and after the fluidized material comes in contact with the surface of the article. The properties of the article are modified because the article has nano-scaled structures distributed on the surface of the article and/or at least partially embedded in the article.

5 Claims, 1 Drawing Sheet

High resolution TEM image of nano-scaled structures on a glass article.

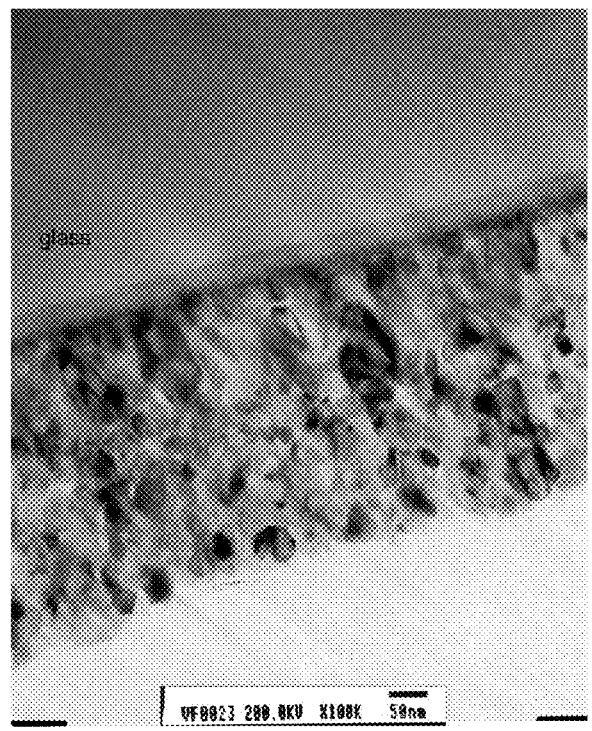
Fig. 1. High resolution TEM image of nano-scaled structures on a glass article.

ARTICLE HAVING NANO-SCALED STRUCTURES AND A PROCESS FOR MAKING SUCH ARTICLE

CROSS-REFERENCE TO RELATED APPLICATIONS

This patent application is a continuation of U.S. application Ser. No. 11/843,756 filed on Aug. 23, 2007 now abandoned, which was a continuation of U.S. application Ser. No. 10/623,401 filed Jul. 18, 2003 (Now Abandoned), which claimed the benefit of U.S. Provisional Application No. 60/397,486 filed on Jul. 19, 2002, and U.S. application Ser. No. 10/623,401 filed on Jul. 18, 2003, all of which applications are herein incorporated by reference.

FIELD OF THE INVENTION

The present invention relates to methods for producing articles that exhibit modified optical, mechanical, and chemical properties; especially methods for producing glass articles containing nano-scaled structures that exhibit modified properties.

BACKGROUND OF THE INVENTION

An article like glass is used for many purposes in today's society. For example, glass articles are used in automotive applications, architectural applications, aerospace applications, etc. Depending on the application, the glass article will need to have different properties. The following are just few examples of the many properties of glass articles: color, transmittance, reflectance, luminescence, bulk or surface electric conductivity, UV/IR absorption, hardness, catalytic (including photocatalytic) surface quality, thermal insulation, photochromic behavior, etc.

One way to obtain a glass article having certain properties is to create a new glass composition. For example, transition metal oxides and metallic colloids have been used to make different glass compositions. The disadvantages of using new glass compositions to achieve different properties are the length of time it takes to change the batch composition in the furnace, the amount of waste generated as a result of changing the batch composition in the furnace, etc. Also, changing the composition of the batch can result in glass that is harder to melt which increases the cost of the production process.

Another way to obtain a glass article having certain properties is to apply a coating composition over the article. Coating compositions for glass articles are well known in the art. Examples of coating compositions include chemical vapor deposition ("CVD") and physical vapor deposition ("PVD") coatings. For example, titanium oxide coatings, fluorine doped tin oxide coatings, and indium doped tin oxide coatings can be applied over glass articles. Several drawbacks are associated with applying a coating composition to a glass article to modify its properties. Such drawbacks include appearance imperfections (coated glass can look different at different angles), chemical and mechanical durability problems, costs, optical refractive index mismatch, etc.

There is a need for a novel method of modifying the properties of various articles like glass that does not have the disadvantages of the conventional methods. The present invention provides a novel method for modifying the optical, mechanical, and/or chemical properties of an article like glass, ceramic or a polymer by including nano-scaled structures on the surface and/or at least partially embedded in the article.

SUMMARY OF THE INVENTION

In a non-limiting embodiment, the present invention is a process for producing an article comprising:
(a) fluidizing a starting material;
(b) forcing the fluidized starting material toward the article, the article having a certain temperature; and
(c) passing the fluidized starting material through a high energy zone, the passing step can occur before the forcing step; after the forcing step but before the fluidizing material comes in contact with the surface of the article; and/or after the forcing step and after the fluidized material comes in contact with the surface of the article, whereby the finished article has nano-scaled structures distributed in the surface of the article and/or at least partially embedded in the article.

In another non-limiting embodiment, the present invention is a three-dimensional article comprising nano-scaled structures distributed on the surface of the article and/or at least partially embedded in the article.

BRIEF DESCRIPTION OF THE DRAWING

FIG. 1 shows a glass article with nano-scaled structures analyzed by a cross-section technique using a JEOL 2000FX transmission electron microscope at 200 kV.

DESCRIPTION OF THE INVENTION

All numbers expressing dimensions, physical characteristics, quantities of ingredients, reaction conditions, and the like used in the specification and claims are to be understood as being modified in all instances by the term "about". Accordingly, unless indicated to the contrary, the numerical values set forth in the following specification and claims may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 7.8, 3 to 4.5, 6.3 to 10.

The terms below are defined herein as follows:

"Deposited over" means deposited or provided on but not necessarily in surface contact with. For example, a coating or material "deposited over" an article does not preclude the presence of one or more other coating films or materials of the same or different composition located between the deposited coating or material and the article.

"Nano-scaled structure"—a three dimensional object having a size ranging from 1 nm to 1000 nm or 1 nm to 500 nm or 1 nm to 100 nm or 1 to 40 nm.

"Opaque" means having a visible light transmittance of 0%.

"Solar control material" refers to a material that affects the solar performance properties of the glass, e.g., transmittance and/or reflectance of electromagnetic radiation, such as in the visible, ultraviolet (UV), or infrared (IR) regions of the electromagnetic spectrum.

"Starting material" refers to a material or mixture of materials that are capable of forming nano-scaled structures.

"Transparent" means having a transmittance through the article of greater than 0% up to 100%.

"Translucent" means allowing electromagnetic energy (e.g., visible light) to pass through but diffusing it such that objects on the other side are not clearly visible.

"Visible light" means electromagnetic energy in the range of 380 nm to 760 nm.

The present invention is a method for producing an article having modified properties comprising the steps of (a) fluidizing a starting material; (b) forcing the fluidized starting material toward the article, the surface of the article having a certain temperature; and (c) passing the fluidized starting material through a high energy zone either before or after the material is forced toward the article.

The first step in the present invention comprises fluidizing a starting material. The following are non-limiting examples of suitable starting materials: organometallics or solutions thereof for example titanium iso-propoxide, titanium iso-propoxide in ethanol, tetraethyl orthosilicate, or tetraethyl orthosilicate in solution; inorganic salts such as hydrogen tetrachloroaurate (III) trihydrate, hydrogen tetrachlorate (III) trihydrate in water, cobalt nitrate, or cobalt nitrate in ethanol; and metal oxides or suspensions thereof such as cerium oxide, cerium oxide in water, zinc oxide, or zinc oxide in ethanol. Further non-limiting examples include:

An aqueous solution comprising noble metal ions. For example, an aqueous solution containing $HAuCl_4.3H_2O$, $AgNO_3$, a copper compound, or mixtures thereof.

A solution containing titanium ion. For example, a solution comprising 0.5-25.0 weight percent of titanium tetra-iso-propoxide dissolved in a mixture of ethanol. 2,4-pentanedione can be added as a stabilizer.

(1) A solution containing antimony and tin ions. For example, a solution comprising monobutyl tin trichloride and antimony trichloride with a $Sb^{3+}/Sn^{4+}$ ratio of 10% which is diluted in ethanol up to 50.0 weight percent and stirred for 30 minutes at room temperature.

Some of the starting materials include nano-scaled structures which are dispersed in solution. Other starting materials do not include nano-scaled structures.

In a non-limiting embodiment, prior to fluidization, the temperature of the starting material can be maintained at a temperature that allows sufficient sublimation or vaporization from a solid or a liquid starting material or at a temperature at which the starting material has a sufficiently low viscosity for atomization, for example, aerosolization of a liquid. In a non-limiting embodiment, the temperature of the starting material can range from room temperature to the boiling temperature of an organometallic liquid.

The starting material can be fluidized in any manner known in the art, including but not limited to, atomizing the starting material into an aerosol; evaporating the starting material into a gas phase; subliming the starting material into a gas phase, or other similar techniques.

For example, in a non-limiting embodiment, the starting material can be put into a commercially available atomizer such as Model 9306A from TSI, Inc. to make an aerosol. The atomizer is operated in a standard manner.

Depending on the specific application, the following characteristics of the aerosol can be varied: aerosol particle size, the aerosol carrier gas, average aerosol droplet (a droplet can be a solid, a liquid, or a combination thereof) size, droplet size distribution of the aerosol, density of the aerosol droplets, flux of aerosol droplets and the aerosol volume output.

In a non-limiting embodiment, the density of the fluidized material can be sufficient for further processing.

Another step in the present invention comprises forcing the fluidized material toward the surface of the article; the surface of the article having a certain temperature. In a non-limiting embodiment, the fluidized material can be forced by imparting momentum to the fluidized materials using a moving gas stream. For example, compressed air, compressed nitrogen, etc. can be used to force the fluidized material toward the surface of the article. In another non-limiting embodiment, the temperature of the moving gas stream can range from room temperature to 2100° F.

A gravitational field, a thermophoretic field, an electrostatic field, a magnetic field or similar can also be used to force the fluidized material toward the surface of the article.

Another step in the present invention comprises passing the fluidized material through a high energy zone. The passing step can be accomplished in a standard manner such as by supplying an additional force or pressure. The passing of the fluidized material step can occur (a) before the forcing step: (b) after the forcing step but before the fluidizing material comes in contact with the surface of the article; and/or (c) after the forcing step and after the fluidized material comes in contact with the surface of the article. In the high energy zone, the fluidized material can be excited using heat, electromagnetic radiation, high voltage or similar to cause the fluidized material to lose volatiles, condense, chemically react, decompose, change phase or a combination thereof.

Examples of suitable high energy zones include, but are not limited to, hot wall reactors, chemical vapor particle deposition reactors ("CVPD"), combustion deposition reactors, plasma chambers, laser beams, microwave chambers, etc.

In a non-limiting embodiment, a hot wall reactor can be the high energy zone. The hot wall reactor is essentially a heated chamber. Starting material can be delivered to the hot wall reactor by a spray system such as a forced aerosol generator. Inside the reactor, the fluidized material can lose volatiles, condense, chemically react, decompose, change phase or a combination thereof.

Without limiting the invention, the following describes some of the typical parameters for the operation of the hot wall reactor in the present invention. Typically, the temperature inside the hot wall reactor ranges from 400° F. to 2100° F. or 900° F. to 1650° F. or 1100° F. to 1400° F. The pressure inside the reactor can be ambient or can be independently controlled. The atmosphere inside the reactor can be nitrogen, air, or a mixture of 2 to 5 percent by volume hydrogen and 95 to 98 percent by volume nitrogen. The residence time (time the material is in the reactor) in the reactor has to be sufficient to enable the requisite processing in the high energy zone to occur.

In another non-limiting embodiment, a CVPD reactor can be the high energy zone. The CVPD is essentially a heated chamber. In a CVPD process, starting material can be evaporated to gas phase as in conventional chemical vapor deposition system. The gas phase can then be forced through the CVPD reactor, for example, as a result of a pressure gradient. Inside the reactor, the fluidized material can lose volatiles, condense, chemically react, decompose, change phase or a combination thereof.

Without limiting the invention, the following describes some typical parameters for CVPD reactor operation in the present invention. Typically, the temperature inside the CVPD can range from 400° F. to 2100° F. or 900° F. to 1650° F. or 1100° F. to 1400° F. The pressure inside the reactor can be ambient or can be independently controlled. The atmosphere inside the reactor can be nitrogen, air, or a mixture of 2 to 5 percent by volume hydrogen and 95 to 98 percent by volume nitrogen. The residence time in the reactor has to be sufficient to enable the requisite processing in the high energy zone to occur.

In yet another non-limiting embodiment, a combustion deposition reactor is the high energy zone. In a combustion deposition reactor, starting material can be atomized, for example, by an aerosol generator to form an aerosol. The aerosol can be introduced into a flame.

The aerosol can be introduced into the flame at any position. At different locations along the flame, the temperature of the flame is different, the chemical make-up of the flame is different, and the velocity of the flame is different.

In the alternative, the aerosol can be mixed in with the gaseous mixture, e.g. air or oxygen or gas, responsible for the flame. The mixture that makes the flame can be a mixture of a combustible material and an oxidizing material such as air and natural gas, oxygen and natural gas, or carbon monoxide and oxygen.

The temperature range of the flame typically can range from 212° F. to 2900° F. or 400° F. to 2300° F. The residence time (time the material is in the flame) has to be sufficient to enable the requisite processing in the high energy zone to occur.

In another non-limiting embodiment, a plasma chamber can be the high energy zone. In the plasma chamber, the fluidized material can be forced through a gas discharge, for example an atmospheric or low pressure plasma, and can be energized through collision with electrons or ions that constitute the plasma. The plasma can comprise a reactive gas like oxygen, an inert gas like argon or a mixture of gases.

The pressure in the plasma chamber can range from 10 mtorr to 760 torr. The residence time in the plasma chamber has to be sufficient to enable the requisite processing in the high energy zone to occur.

For example, the plasma chamber can be a stainless steel chamber in which a gaseous phase is excited to form a plasma.

In a further non-limiting embodiment, a laser beam can be the high energy zone. The fluidized material can pass through the laser beam and absorb photons. A suitable laser includes, but is not limited to, a $CO_2$ laser with a wavelength of 10,600 nm. See U.S. Pat. No. 6,482,374 which is hereby incorporated by reference for an example of a suitable laser.

The fluidized material can be forced to the surface of various articles. Suitable articles for the present invention include, but are not limited to, polymers, ceramics and glass. The article can be glass; especially window glass made by the float process. The glass can be of any type, such as conventional float glass or flat glass, and can be of any composition having any optical properties, e.g., any value of visible transmission, ultraviolet transmission, infrared transmission, and/ or total solar energy transmission. Examples of suitable glass include borosilicate glass and soda-lime-silica glass compositions which are well known in the art. Exemplary glass compositions are disclosed in, but are not limited to, U.S. Pat. Nos. 5,071,796; 5,837,629; 5,688,727; 5,545,596; 5,780,372; 5,352,640; and 5,807,417.

Suitable ceramic articles include oxides such as alumina, zirconia, and clay and non-oxides such as silicon carbide and alumina nitride.

Suitable polymers include polymethylmethacrylate, polycarbonate, polyurethane, polyvinylbutyral (PVB) polyethyleneterephthalate (PET), or copolymers of any monomers for preparing these, or mixtures thereof.

Just before (up to 1 second prior) the fluidized material comes in contact with the surface of the article, the temperature of the surface of the article can range from 25° F. to 3000° F. For glass articles, the temperature typically can range from 700° F. to 2100° F. or 1100° F. to 1900° F. or 1500° F. to 1760° F. For polymer articles, the temperature typically can range from 25° F. to 600° F. The temperature of the article is one of the factors that determine how far the nano-scaled structures will penetrate into the article.

After the fluidized material comes in physical contact with the surface of the article, nano-scaled structures will be present on the surface and/or at least partially embedded in the finished article. The nano-scaled structures can be bonded to the surface of the article by chemical or mechanical bonding. The nano-scaled structures can be incorporated into the body of the article by the convective flow of glass, diffusion, or other processes if the viscosity of the article is sufficiently low.

The process of the present invention can also comprise optional steps. For example, various coatings can be applied on the article at different points in the process. For example, if the article is glass, an anti-reflective coating or a conductive film can be applied to the article before or after the fluidized material is forced toward the surface of the article. As another example, an alcohol based solution of titanium iso-propoxide can be sprayed on the surface of the article before or after the fluidized material is forced toward the surface of the article.

Also, the invention can include steps related to heating and/or cooling the article. For example, the article can be heated to change the nano-scaled structures or form, for example, bend or laminate, the final article. Processes such as bending or tempering can serve as a high energy zone as described above. The article can be heated to a temperature to at least partially dissolve the nano-scaled structures or increase the depth of penetration of the nano-scaled structures in the article. Also, the article can be cooled to produce annealed glass as is well known in the art.

The process of the present invention will result in the formation of a three dimensional article having nano-scaled structures (a) retained on the surface or partially embedded in the article, (b) at least partially embedded in the article, or (c) fully or partially dissolved in the article. See FIG. 1 for an example of an article produced according to the present invention. The nano-scaled structures can be located on the surface of the article and/or up to 100 micrometers below the surface of the article or up to 20 micrometers below the surface of the article. The nano-scaled structures can be distributed in various ways throughout the depth of the article. For example, 100 percent of the nano-scaled structures can be on the surface of the article. The article can include solid nano-scaled structures and/or dissolved nano-scaled structures. The nano-scaled structures can have the following shapes: spherical, polyhedral like cubic, triangular, pentagonal, diamond shaped, needle shaped, rod shaped, disc shaped etc. The nano-scaled structures can have an aspect ratio of 1:1 to 1:500 or 1:1 to 1:100. The nano-scaled structures can have a degree and orientation of crystallinity ranging from completely amorphous (0 percent crystallinity) to fully orientated along one crystal orientation. The nano-scaled structures can be in contact with each other or separated by a distance of from 1 nm to 1000 nm Depending on the type of nano-scaled structures, the orientation of the nano-scaled structures, the degree of embeddedness of the nano-scaled structures in the article, etc, various properties of articles can be modified. For example, the reflectivity of the article can be selectively increased or decreased. The hardness of the article can be increased. The catalytic property of the article can be increased. The color of the article can be changed. The UV/IR penetration of the article can be decreased. The surface area of adhesion for the article can be increased. The scattering of the article can be increased for use in, for example, a higher quantum efficiency photovoltaic device.

It is envisioned that the process of the present invention will be used as part of an on-line production system. For example, the process of the present invention can be part of a float glass operation where the process is performed near the hot end of a conventional float bath. The invention is not limited to use with the float process. For example, the invention can in a vertical draw process.

The process of the invention has several benefits. First, the invention eliminates costly down-stream process steps because the invention can be part of an on-line process. Second, the invention has a short change time because it can be quickly implemented. Third, the invention produces a durable article due to the high temperatures utilized. Fourth, the invention allows the degree of agglomeration of the nano-scaled structures to be controlled. Fifth, the invention can be combined with other processes like CVD, spray pyrolysis, and off-line techniques like PVD processes.

EXAMPLES

The present invention will now be illustrated by the following, non-limiting examples.

The following examples show how suitable starting materials were made.

Examples of Starting Materials

Example 1

5.0 g of titanium iso-propoxide was mixed into a mixture of 7.0 g of 2,4-pentanedione and 88.0 g of reagent alcohol while stirring at room temperature for 30 minutes.

Example 2

In a solution already prepared in Example 1 with 5 wt % concentration of titanium iso-propoxide, 0.084 g of anatase titanium dioxide nanocrystals (ST-01, average size 7 nanometer) from Ishihara Sangyo Kaiha in Japan was added slowly while vigorously stirring at room temperature.

Example 3

In a solution already prepared in Example 1 with 5 wt % concentration of titanium iso-propoxide, 2.8 g of a solution consisting of 3.0 wt % brookite titanium dioxide nanocrystals in an alcohol solution (NTB-13) from Showa Denko K. K. in Japan was added slowly while vigorously stirring at room temperature.

Example 4

In a solution already prepared in Example 1 with 5 wt % concentration of titanium iso-propoxide, 0.05 g of monobutyl tin trichloride was added slowly while stirring at room temperature.

Example 5

1 g of antimony chloride and 9 g of monobutyl tin trichloride were added to 90 g of reagent alcohol while stirring at room temperature.

Example 6

0.1 g hydrogen tetrachloroaurate (III) trihydrate (HAuCl4.3H$_2$O) was dissolved in 100 g of deionized water resulting in a yellowish transparent solution. The resultant solution was stored in an opaque container until used.

Example 7

500 g of titanium iso-propoxide.

Example 8

500 g of tetraethyl orthosilicate.

Example 9

5 g of tetraethyl orthosilicate (TEOS) was mixed into 95 g of reagent alcohol while stirring.

Example 10

1 g of Altium™ TiNano 40 anatase nanoparticles from Altair Nanomaterials Inc. (Reno, Nev.) was dispersed in 99 g of deionized water while stirring at room temperature. The mixture was ultrasonically agitated for 30 minutes.

Example 11

10 g of NanoTek® nanopowdered cerium oxide purchased from Nanophase Technologies Corporation (Romeoville, Ill.) was dispersed in 90 g of deionized water while stirring at room temperature. The mixture was ultrasonically agitated for 30 minutes.

Example 12

A 15 wt. % NanoTek® nanopowdered zinc oxide in reagent alcohol dispersion was purchased from Nanophase Technology Corporation (Romeoville, Ill.). The material was ultrasonically agitated for 2 hours to deagglomerate the as-received material.

Example 13

5.0 g of cobalt nitrate was dispersed in 95 g of reagent alcohol. The solution was stirred at room temperature for 30 minutes and ultrasonically treated for 10 minutes.

Example 14

10.0 g of cerium acetate was dispersed in 45 g of reagent alcohol and 145 g of deionized water. The solution was stirred at room temperature for 30 minutes and ultrasonically treated for 10 minutes.

Example 15

10.0 g of a cerium nitrate was dispersed in 90 g of reagent alcohol. The solution was stirred at room temperature for 30 minutes and ultrasonically treated for 10 minutes.

Example 16

10 g of alumatrane (N(CH$_2$CH$_2$O)3Al, approx. 10% CY) as made by TAL Materials (Ann Arbor, Mich.) was mixed with 90 g of reagent alcohol while stirring.

Example 17

As in example 10, but the material was zirconia nanoparticles from TAL Materials (Ann Arbor, Mich.).

Example 18

While stirring at room temperature, 20 g of 3.0 wt % brookite titanium dioxide nanocrystals in an alcohol solution (NTB-13) from Showa Denko K. K. in Japan was added to a solution of 2.4 g titanium isopropoxide mixed with 3.4 g 2,4-pentanedione in 74.2 g of reagent alcohol.

Performance Examples

In the following examples the starting material was atomized to a stream of aerosol using a single jet atomizer (Model 9302A) from TSI Incorporated (St. Paul, Minn.) with a nitrogen gas input pressure of either 25 or 40 Psi (corresponding to an output of 6.6 or 9.2 L/min.) In some cases, multiple generators were used simultaneously to produce a larger output. The atomizing gas could either be nitrogen or compressed air.

The article to be modified was generally heated in the nitrogen atmosphere of a conveyor furnace. The conveyor speed could be varied from 1 to 10"/minute. In a few instances glass was preheated in furnace, moved to the benchtop and then modified in air for a specified period of time.

The combustion burner for combustion modification was a water-cooled, surface mixing combustion burner where the aerosol was introduced into the combustion space either by being mixed in with the natural gas stream or by being injected through orifices on the burner face.

In Table 1, properties of nano-scaled structures are shown. The nano-scaled structures were produced in the following manner. The mixtures of examples 1, 5, 9, 10, 16, and 17 were atomized (6.6 L/min.) with nitrogen and mixed into an oxygen-gas (ratio of 2.3:1) combustion flame in an air atmosphere. Nanoparticles were collected for 1 minute onto copper grids at the tip of the flame visible to the naked eye.

The nano-structures were analyzed using a Transmission Electron Microscope "TEM" (JEOL 2000FX TEM at an accelerating voltage of 200 kV).

Table 2 shows the modified color properties of articles that were produced according to the present.

Article 1 was prepared in the following manner: The starting material of Example 6 was atomized with a nitrogen gas input pressure of 40 Psi. The stream of aerosol was then forced by a compressed air with a pressure of 20 Psi into the hot wall reactor with a length of 17", whose temperature was set at 1300° F. The PPG Starphire® glass article was stationary and its temperature was also set at 1300° F. The forced aerosol spray process lasted for 1 min. Gold nano-scaled structures were deposited on the surface of colorless PPG Starphire® glass article after passing the hot wall reactor. The finished PPG Starphire® glass article with gold nano-scaled structures was obtained after cooling to room temperature. The color of the said PPG Starphire® glass article with gold nano-scaled structures was pink.

Article 2 was formed in the following manner: The above said glass article with gold nano-scaled structures was also coated with titania coatings using the starting material from Example 1. The deposition process was as follows. The starting material of Example 1 was atomized with a nitrogen gas input pressure of 40 Psi. The stream of aerosol was then forced by a compressed air with a pressure of 20 Psi into the hot wall reactor with a length of 17", whose temperature was set at 1140° F. The PPG Starphire® glass article with gold nano-scaled structures was stationary and its temperature was also set at 1140° F. The forced aerosol spray process lasted for 1 min. Titania coatings were deposited on the surface of above said PPG Starphire® glass article with gold nano-scaled structures after passing the hot wall reactor. The final PPG Starphire® glass article with gold/titania nano-scaled structures was obtained after cooling to room temperature. The color of the said PPG Starphire® glass article with gold/titania nano-scaled structures was blue-green. The gold nano-scaled structures and gold/titania nano-scaled structures were confirmed by a LEO 1530 scanning electron microscope and its attached energy dispersive spectroscopy, and X-ray diffraction using Philips X'Pert MPD X-ray diffractometer from PANalytical (Natick, Mass.).

Article 3 was formed in the following manner: Example 13 was atomized at 19.8 L/min. with nitrogen and introduced into an oxygen-gas flame (ratio of 4.6:1) which was incident upon Starphire® glass heated to approximately 750° C. in a nitrogen atmosphere and moving at 2"/minute through the furnace. The result was the incorporation of cobalt into the glass surface. A striking blue color was produced. Transmission was measured using a Lamda 9 spectrophotometer produced by Perkin Elmer. The color was computed using the L*a*b* system using CIELAB Color (D65, 10°).

Table 3 shows the modified conductivity of articles that were produced according to the present invention.

Article 4 was prepared in the following manner: Example 1 was atomized at 6.6 L/min. with nitrogen, injected into an oxygen-gas flame (ratio of 4.6:1) which was incident upon clear glass heated to approximately 550° C. and moving at 4"/minute in a nitrogen atmosphere. After the glass cooled, it was coated with approximately 1800 Å thick tin oxide film applied by spray pyrolysis. The resultant sample had a rough, conductive surface, indicating that the roughness, as exemplified by the haze level, did not result in a significant drop in conductivity. Haze was measured by a HazeGardPlus made by BykGardner.

Table 4 shows the modified texture of articles that were produced according to the present invention.

Articles 5, 6, 7 were prepared in the following manner: Example 9 was atomized (from 19.8 to 36.8 L/min. with either nitrogen or compressed air and introduced into an oxygen-gas flame (ratio of 6.1:1) which was incident upon Starphire® glass heated to approximately 650° C. moving at either 5 or 10"/minute in a nitrogen atmosphere. This resulted in silica nanoparticles adherent to the glass surface. Samples were produced with varying degrees of roughness by varying the atomization output, atomization gas, and conveyor speed.

Article 8 was prepared in the following manner: The starting material from Example 5 was atomized with a nitrogen gas input pressure of 40 Psi. The stream of aerosol was then forced by a compressed air with a pressure of 40 Psi into the hot wall reactor with a length of 17", whose temperature was set at 1260° F. The PPG clear glass article was moving at a speed of 3"/min and its temperature was set at 1260° F. Antimony doped tin oxide nano-scaled structures were deposited on the surface of moving PPG clear glass article after passing the hot wall reactor. The finished PPG clear glass article with antimony doped tin oxide nano-scaled structures was obtained after cooling to room temperature.

Article 9 was prepared in the following manner: The starting material of Example 1 was atomized with a nitrogen gas input pressure of 40 Psi. The stream of aerosol was then forced by a compressed air with a pressure of 60 Psi into the hot wall reactor with a length of 17", whose temperature was set at 1260° F. The PPG clear glass article was moving at a speed of 1"/min and its temperature was set at 1260° F. Titania nano-scaled structures were deposited on the surface of moving PPG clear glass article after passing the hot wall reactor. The finished PPG clear glass article with titania nano-scaled structures was obtained after cooling to room temperature.

The textured surface was measured using Digital Instruments NanoScope Atomic Force Microscopy with an image statistical data of RMS.

Table 5 shows the modified reflectance ("anti-glare") properties of articles produced according to the present invention.

Article 10 was prepared in the following manner: The starting material of Example 8 in a glass container with a temperature of 194° F. was evaporated to its gas phase by bubbling with compressed nitrogen gas. The gas phase was fed in to a CVPD reactor whose temperature was set at 1380° F. The gas phase was forced to move faster inside the CVPD reactor by a compressed air with a pressure of 10 Psi. The gas phase decomposed inside the CVPD reactor to form white species. These white species were thereafter forced by the compressed air through the CVPD reactor and toward a PPG clear glass article with a size of 4"×4", whose temperature was set at 300° F. Thereafter, the PPG clear glass article with white species was heated to 1380° F. for 30 min. After cooling to room temperature, a PPG clear glass article with silica nano-scaled structures was obtained. The silica nano-scaled structures was observed using a LEO 1530 scanning electron microscope and a 10 keV accelerating voltage.

Anti-glare property is represented by a reduction of surface reflectance of an object. The reflectance at 65° angle of incidence was measured by WVASE32 Spectroscopic Ellipsometer from J. A. Woollam Co., Inc. (Lincoln, Nebr.). In Table 5, the PPG clear glass article with silica nano-scaled structures in this invention has only half of integrated reflectance at 65° angle of incidence in comparison to PPG clear glass article without silica nano-scaled structures.

Table 6 shows the modified UV properties of articles that were produced according to the present invention.

Article 11 was prepared in the following manner: Example 15 was atomized (19.8 L/min.) with nitrogen and introduced into a oxygen-gas flame (ratio of 4.6:1) which was incident upon glass heated to 800° C., resulting in the incorporation of cerium into the glass surface. X-ray fluorescence showed approximately 4 wt % Ce incorporated into the glass. A decrease in the UV transmission was noted, with minimal change in the visible and IR portions of the spectrum. Transmission was measured using a Lamda 9 spectrophotometer produced by Perkin Elmer.

Table 7 shows the modified hydrophilic character of articles that were produced according to the present invention.

Article 12 was prepared in the following manner: Example 1 was atomized (6.6 L/min.) with nitrogen, injected into an oxygen-gas flame (ratio of 2.3:1) which was incident upon clear glass at approximately 1800° F. for 2 minutes in air. Titanium dioxide nanoparticles were deposited into the surface region of the hot glass. X-ray diffraction by a Philips X'Pert MPD X-ray diffractometer from PANalytical indicated the presence of rutile titania nanoparticles. Scanning electron microscopy of the glass surface revealed the presence of a many uniformly-sized titania particles less than 50 nm in diameter. The incorporation of the titania at the glass surface gave rise to UV-induced hydrophilicity.

Article 13 was prepared in the following manner: Example 18 was atomized (36 L/min.) with nitrogen and pushed toward Starphire® glass heated to approximately 675° C. in a nitrogen atmosphere. For this sample, there was no flame; the aerosol was produced and kept to less than 200° F. until it was within 3 inches of the top surface of the article.

Article 14 was prepared in the following manner: The starting material of Example 1 was atomized with a nitrogen gas input pressure of 40 PSI. The stream of aerosol was then forced by a compressed air with a pressure of 60 PSI into the hot wall reactor with a length of 17", whose temperature was set at 1260° F. The PPG clear glass article was moving at a speed of 2"/min and its temperature was set at 1260° F. Titania nano-scaled structures were deposited on the surface of moving PPG clear glass article after passing the hot wall reactor. The finished PPG clear glass article with titania nano-scaled structures was obtained after cooling to room temperature. The titania nano-scaled structures was confirmed by a LEO 1530 scanning electron microscope and its attached energy dispersive spectroscopy. The anatase titania crystal phase was determined by Philips X'Pert MPD X-ray diffractometer from PANalytical (Natick, Mass.).

UV-induced hydrophilicity was characterized by monitoring the decrease of water contact angle on the article surface as a function of UV exposure time (UVA is 340 nm at 28 W/m2 or UVC is 254 nm).

Table 8 shows the modified photocatalytic activity of articles that were produced according to the present invention.

Article 15 was prepared in the following manner: The starting material of Example 1 was atomized to a stream of aerosol using a Six-Jet Atomizer (Model 9306A) from TSI Incorporated (St. Paul, Minn.) with a nitrogen gas input pressure of 40 PSI. The stream of aerosol was then forced by a compressed air with a pressure of 60 PSI into the hot wall reactor with a length of 17", whose temperature was set at 1260° F. The PPG clear glass article was moving at a speed of 2"/min and its temperature was set at 1260° F. Titania nano-scaled structures were deposited on the surface of moving PPG clear glass article after passing the hot wall reactor. The finished PPG clear glass article with titania nano-scaled structures was obtained after cooling to room temperature. The titania nano-scaled structures was confirmed by a LEO 1530 scanning electron microscope and its attached energy dispersive spectroscopy. The anatase titania crystal phase was determined by Philips X'Pert MPD X-ray diffractometer from PANalytical (Natick, Mass.).

Photocatalytic activity (PCA) was measured from the articles with titania nano-scaled structures in this invention towards the degradation of stearic acid by monitoring the decrease of integrated IR absorbance in the —CH2 stretching model as a function of UVA-340 exposure time at 28 W/m2. The IR absorbance in the —CH2 stretching model was measured using an ATI Mattson Infinity Series FTIR spectroscopy from Thermo Mattson (Madison, Wis.). The slope of this plot is designated as the photocatalytic activity (PCA). As shown in Table 1, the articles with titania nano-scaled structures in this invention has a new function of photocatalytic activity at a level of $71 \times 10-3$ cm$-1 \cdot$min$-1$ compared to PPG clear glass without titania nano-scaled structures, which has no photocatalytic property.

TABLE 1

Properties of nano-scaled structures according to the Present Invention

| Material | Particle Size (nm) (measured in TEM) | Comments |
|---|---|---|
| Example 1 | 10 nm | |
| Example 5 | 20 nm | |
| Example 9 | 20 nm | |
| Example 16 | <20 nm >500 nm | Wide size distribution |
| Example 10 | <100 nm | Many small particles and agglomerates |
| Example 17 | >500 nm | Agglomerates of various sizes |

TABLE 2

Color Properties of Articles of the Present Invention

| Color | Colorless | Pink | Blue-green |
|---|---|---|---|
| Test Specimen | Starphire ® glass | Article 1 | Article 2 |
| Thickness (") | 0.1267 | 0.1267 | 0.1267 |
| L* | 96.58 | 91.86 | 81.23 |
| a* | −0.13 | 6.60 | −18.96 |
| b* | 0.11 | −2.10 | −8.82 |

| Color | Colorless | Blue |
|---|---|---|
| Test Specimen | Starphire ® glass | Article 3 |
| Thickness (") | 0.1548 | 0.1548 |
| L | 96.51 | 81.89 |
| a* | −0.17 | −1.47 |
| b* | 0.1 | −20.81 |

TABLE 3

Conductivity of articles of the Present Invention

| | Haze | Resistance (Ω) |
|---|---|---|
| Control | 2 | 99 |
| Article 4 | 19 | 86 |

TABLE 4

Texture of articles of the Present Invention

| Test Specimen | RMS (nm) |
|---|---|
| PPG clear glass control sample | 0.33 |
| Article 5 | 0.95 |
| Article 6 | 4.2 |
| Article 7 | 11.9 |
| Article 8 | 16.45 |
| Article 9 | 15.97 |

TABLE 5

Reflectance ("Anti-glare") Properties of Articles of the Present Invention

| Test Specimen | Integrated reflectance at 65° angle of incidence (%) |
|---|---|
| Article 10 | 7.24 |
| Control | 14.62 |

TABLE 6

UV Properties of Articles of the Present Invention
Change in transmission characteristics for PPG Clear glass ("control") and Article 11

| | UV (ISO 9050, 280-380 nm) | Visible (ASTM 891, 2°) | IR (ASTM 891, 800-2500 nm) | Total Solar (SAE, 300-2500 nm) |
|---|---|---|---|---|
| % Δ Transmission (% Δ = (Article 11 − control)/control) | −14% | −2% | −1% | −2% |

TABLE 7

Hydrophilic Character of Articles of the Present Invention

| | PPG Clear glass | Titania-treated glass) |
|---|---|---|
| Article 12: Contact angle with water after 6 hours of UVA exposure | 26 | 7 |
| Article 13: Contact angle with water after 12 hours of UVC exposure | 23 | 2 |

| UVA-340 exposure time (min) | PPG clear glass | Article 14 |
|---|---|---|
| 0 | 34 | 32.7 |
| 5 | 45 | 28.3 |
| 15 | 40 | 7.7 |
| 25 | 44 | 7.7 |
| 35 | 43 | 6.3 |
| 45 | 48 | 6.7 |
| 60 | 40 | 5 |

TABLE 8

Photocatalytic Activity of Articles of the Present Invention

| | PPG clear glass | Article 15 |
|---|---|---|
| PCA ($\times 10^{-3}$ cm$^{-1}$ · min$^{-1}$) | 0 | 71 |

CONCLUSION

By utilizing the process of the present invention, the following properties of the sample articles could be changed: color, conductivity, UV absorption, reflectivity, photocatalytic ability, etc.

It will be readily appreciated by those skilled in the art that modifications can be made to the invention without departing from the concepts disclosed in the foregoing description. Such modifications are to be considered as included within the scope of the invention. Accordingly, the particular embodiments described in detail hereinabove are illustrative only and are not limiting as to the scope of the invention, which is to be given the full breadth of the appended claims and any and all equivalents thereof.

We claim:

1. A process for producing an article, comprising:
   fluidizing a solution comprising at least one of inorganic or organic compounds by at passing the fluidized material through a high energy zone selected from the group consisting of a hot wall reactor or a combustion reactor; and forcing the fluidized material toward a glass substrate using a moving gas stream, the glass substrate having a temperature between 700° F. and 2100° F., wherein a finished article has nano-scaled structures distributed in a surface of the glass substrate or at least partially embedded in the glass substrate.

2. The process of claim 1, wherein the solution is selected from solutions comprising at least one of titanium iso-propoxide, tetraethyl orthosilicate, hydrogen tetrachloroaurate (III) trihydrate, cobalt nitrate, and metal oxides.

3. The process of claim 2, wherein the metal oxides are selected from oxides of cerium, titanium, zinc, and mixtures thereof.

4. The process of claim 1, wherein the solution comprises nano-scaled structures.

5. The process of claim 1, wherein the process is an on-line production process.

\* \* \* \* \*